United States Patent
Heffelfinger (10) Patent No.: US 10,080,630 B2
(45) Date of Patent: *Sep. 25, 2018

(54) METHOD OF MAKING A DENTURE WITH NATURE BITE AND WEAR PROPERTIES AND DENTURE

(71) Applicant: Bite Innovations, LLC, Auburn, IN (US)

(72) Inventor: Nathaniel Heffelfinger, Auburn, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/600,820

(22) Filed: May 22, 2017

(65) Prior Publication Data
US 2017/0252133 A1 Sep. 7, 2017

Related U.S. Application Data

(63) Continuation-in-part of application No. 14/743,107, filed on Jun. 18, 2015, now Pat. No. 9,655,700.

(51) Int. Cl.
| A61C 13/097 | (2006.01) |
| A61C 13/00 | (2006.01) |
| A61C 13/10 | (2006.01) |

(52) U.S. Cl.
CPC ...... *A61C 13/0004* (2013.01); *A61C 13/0024* (2013.01); *A61C 13/097* (2013.01); *A61C 13/10* (2013.01)

(58) Field of Classification Search
CPC . A61C 13/0004; A61C 13/0027; A61C 13/10; A61C 13/083
See application file for complete search history.

(56) References Cited

U.S. PATENT DOCUMENTS

| 4,302,187 A | 11/1981 | Yoon |
| 4,642,052 A | 2/1987 | Carlson |
| 5,678,993 A | 10/1997 | Jeffer et al. |
| 6,056,546 A | 5/2000 | Van Handel |
| 7,153,135 B1 | 12/2006 | Thomas |
| 9,655,700 B2* | 5/2017 | Heffelfinger ......... A61C 13/097 |
| 2005/0112523 A1 | 5/2005 | Massad |
| 2006/0099552 A1* | 5/2006 | van der Zel ....... A61C 13/0003 |
| | | 433/223 |
| 2009/0104585 A1* | 4/2009 | Diangelo ............ A61C 8/0001 |
| | | 433/223 |
| 2012/0322031 A1 | 12/2012 | Kim |

(Continued)

FOREIGN PATENT DOCUMENTS

| CN | 102178564 A | 9/2011 |
| CN | 103770223 A | 5/2014 |

OTHER PUBLICATIONS

Joanne M. Livaditis et. al., The Use of Custom-Milled Zirconia Teeth to Address Tooth Abrasion in Complete Dentures; A Cliniical Report, 22 Journal of Prosthodontics 208-213, published 2013, passim.

(Continued)

*Primary Examiner* — Julianna N Harvey (57) ABSTRACT

The present invention to a method of denture manufacture that incorporates CAM-formed zirconia teeth or zirconia tooth segment members, resulting in a natural fit, feel, and wear essentially equivalent to the wear properties of natural teeth, with wear and durability properties superior to dentures known in the art.

19 Claims, 5 Drawing Sheets

(56) References Cited

U.S. PATENT DOCUMENTS

2013/0101962 A1    4/2013  Howe
2013/0316302 A1  11/2013  Fisker
2015/0182316 A1*  7/2015  Morales ................. A61C 13/01
                                                                       433/199.1

OTHER PUBLICATIONS

Office Action dated Oct. 5, 2017 in U.S. Appl. No. 15/486,139, Method of Making a Denture With Natural Bite and Wear Properties and Denture by Nathaniel Heffelfinger et. al.

* cited by examiner

METHOD OF MAKING A DENTURE WITH NATURE BITE AND WEAR PROPERTIES AND DENTURE

CROSS-REFERENCES TO RELATED APPLICATIONS

This Application is a continuation-in-part of U.S. patent application Ser. No., 14/743,107, Making a Denture With Natural Bite and Wear Properties and Denture, filed on Jun. 18, 2015, and incorporates the same in its entirety by reference herein.

STATEMENT REGARDING, FEDERALLY SPONSORED RESEARCH OR DEVELOPMENT

Not applicable

BACKGROUND

This invention relates a method of making an artificial full or partial denture with natural bite and wear properties.

Full and partial artificial dentures are well known to the art. A full or partial denture is defined herein as a removable implantable structure overfilling all or part of the upper gums with some or all teeth removed, or all or part of the lower gums with some or all teeth removed, and providing occlusal surfaces that can be used for chewing in lieu of natural teeth. Also known to the art are bridge dentures, in which all or part of a full or partial denture overfits or is supported by existing tooth structure or existing implants, rather than the upper or lower gums.

It is a longstanding goal of dentists and other professionals involved in denture manufacture to create dentures that, when worn, feel and fit as similar as possible to the patient's natural teeth. To obtain this feel and fit, defined herein as "natural," it is necessary to create dentures that, when used, result in a resting jaw position, bite pattern, occlusal contact, and relative tooth movement as similar as possible to that of the patient's natural teeth. This will be referred to herein as the patient's "natural bite." For dentures to maintain a natural bite feel, it is further necessary for artificial teeth within the denture to wear at a rate similar to the wear rate of natural teeth, and in any event to wear at a rate superior to the wear rate of conventional dentures known to the art.

The first step in one common method of denture manufacture involves assessment by the dentist of the patient's natural bite or desired bite. Such assessment is typically conducted by measuring the patient's jaw and collecting preliminary impressions of landmark structures in the patient's mouth. These preliminary impressions are used to create a custom impression tray. A denturist or other skilled artisan often makes the custom impression tray. The patient is then fitted with the custom impression tray for more detailed functional impressions of the patient's oral structures, and for assessment of the patient's muscle movements during speech and mastication. The dentist next performs occlusal registration, commonly using wax bite registration, tactile bite registration, intro-oral pin tracing, or gnathometer bite registration techniques. Next, the dentist selects artificial teeth of desired size and shape for attachment to that base. The size and shape of the artificial teeth is selected to most closely replicate the patient's natural or desired bite, as determined by the measurements data collected during the assessment.

The selected artificial teeth are then set in wax try-in base for a test fitting with the patient. Alternatively, the artificial teeth may be removably inserted into a base, such as an acrylic base, intended as the permanent base. The patient provides feedback on the fit and feel of the denture, and the dentist makes any necessary adjustments to the parameters of the base, as well as to the size, shape, and placement of the artificial teeth. Once the patient is satisfied with the look and feel of the try-in denture, a permanent denture is made by attaching the artificial teeth to a permanent base.

As can be seen, manufacturing dentures to achieve a natural bite feel for the patient is a time and labor intensive process. The manufacture of dentures generally involves an iterative process of test-fitting and reshaping, and involve the time of both a dentist and the time of a skilled denturist or other artisan. A patient may require three, four, five, or even more test-fittings before the denture is satisfactorily shaped and sized.

It is known to the art to increase the precision of the denture manufacture process through the use of computer-aided drawing (CAD) software, often linked to milling, cutting, or other shaping machines capable of forming material in accordance with instructions delivered by CAD software. Such machines will be referred to herein as computer-aided manufacture (CAM) machines. For example, it is known to the art to use a haptic device to allow a computer to create a three-dimensional digital CAD model of a denture based on the patient's oral structures. An actual denture replicating the three-dimensional model can then be made using a CAN machine linked to the CAD program. It is also known to the art for the dentist or denturist to use data collected during assessment to create a three-dimensional CAD model of a denture approximating the patient's oral structure, or containing other desired parameters or characteristics. An actual denture replicating the three-dimensional model can then be made using a CAM machine linked to the CAD program. It is also known to the art for the dentist or denturist, to fabricate a denture based on information collected during assessment, and then to create a three-dimensional digital model of that actual denture for record purposes, such as through CAD scanning.

It is known to the art to use CAD models, in conjunction with CAM machines, most notably milling machines, to aid in the precise manufacture of custom denture bases, which often include custom-milled sockets to replicate the natural spacing and placement of the patient's teeth. These sockets can then be fitted with selected commercially available artificial teeth, or with custom manufactured artificial teeth. The patient can then undergo the iterative process of test-fitting, providing feedback, and further alteration of the denture to achieve proper occlusion and a satisfactory overall feel.

It is known to use plastic as a material for artificial teeth. Plastic artificial teeth are commonly available, relatively inexpensive, and easy to shape and otherwise work with. Plastic teeth can also be easily made with to resemble real teeth. Plastic artificial teeth suffer two notable drawbacks. First, plastic artificial teeth are molded, and thus are not consistently sized. Plastic teeth are commonly made from molds with a long service life. Over the course of the mold's service life, material from the wall of the mold wears away, resulting in an increase in the size of the mold cavity. A plastic tooth made from a mold that has been in service for ten years will therefore commonly be larger than a plastic tooth made from that same mold when the mold was new. Additionally, molds contain multiple cavities, and the mold-to-mold wear is not necessarily uniform. Thus, while a dentist may select artificial teeth of a certain purported size based on the listed size of the mold used to make it, the actual size of the tooth may vary from the listed size specifications, even if the same mold is used over time. This variation and uncertainty increases the likelihood that the denture will not be ideally shaped or sized immediately upon adding the artificial teeth, and increases the likelihood that adjustments will be required. Second, plastic teeth wear at significantly quicker rate than natural teeth or teeth restored using porcelain or metal materials. Over time, as the plastic teeth wear more rapidly, any natural bite feel accomplished by the original denture can be altered or lost. Further, the wear of plastic teeth may lead to changes in jaw relation and/or altered fit of the prosthesis, which may cause patient discomfort and may weaken the prosthesis, leading to potential fracture and failure. Third, denture teeth often oppose natural teeth or crowns that are unevenly positioned or worn into a suboptimal shape or configuration. Plastic teeth are not optimally configured or shaped to oppose the unique surfaces encountered in a user's mouth, and hand-shaping each plastic tooth is a difficult and time intensive process.

It is known to the art to address the problems posed by the inconsistent sizing and rapid wear of plastic artificial teeth by using metal occlusal inserts, crowns, or overlays. These inserts, crowns, or overlays, however, have poor esthetics and ruin the appearance of real teeth that many patients desire from dentures.

The present invention is directed to a method of denture manufacture that incorporates CAM-formed teeth made of zirconia (also referred to herein as zirconium). Embodiments of the present method are used to manufacture dentures that are more easily shaped and sized to create a natural bite feel, retain the esthetics of natural teeth, and prevent uneven wear between the artificial teeth and the patient's pre-existing natural or restored teeth, and have improved durability and longevity compared to dentures known to the art. Generally, embodiments of the present invention include a method comprising the steps of:

a. Evaluating a patent to determine desired denture parameters;
 b. Fabricating a first denture according to those desired denture parameters, the first denture including a denture base, optionally made of wax, and polymer denture teeth;
 c. Electronically storing the three-dimensional shape and size of the first denture;
 d. Discarding said polymer denture teeth;
 e. Preparing one or more zirconia denture teeth where the one or more zirconia denture teeth are sized and shaped to create a denture approximating the desired denture parameters when mated to the denture base; and
 f. Attaching said one or more zirconia denture teeth to said denture base to create a useable second denture, where the second denture approximates said desired denture parameters.

BRIEF DESCRIPTION OF THE DRAWINGS

These and other features, aspects, and advantages of the present invention will become better understood with regard to the following description and accompanying drawings, where.

DETAILED DESCRIPTION

Figure 1:
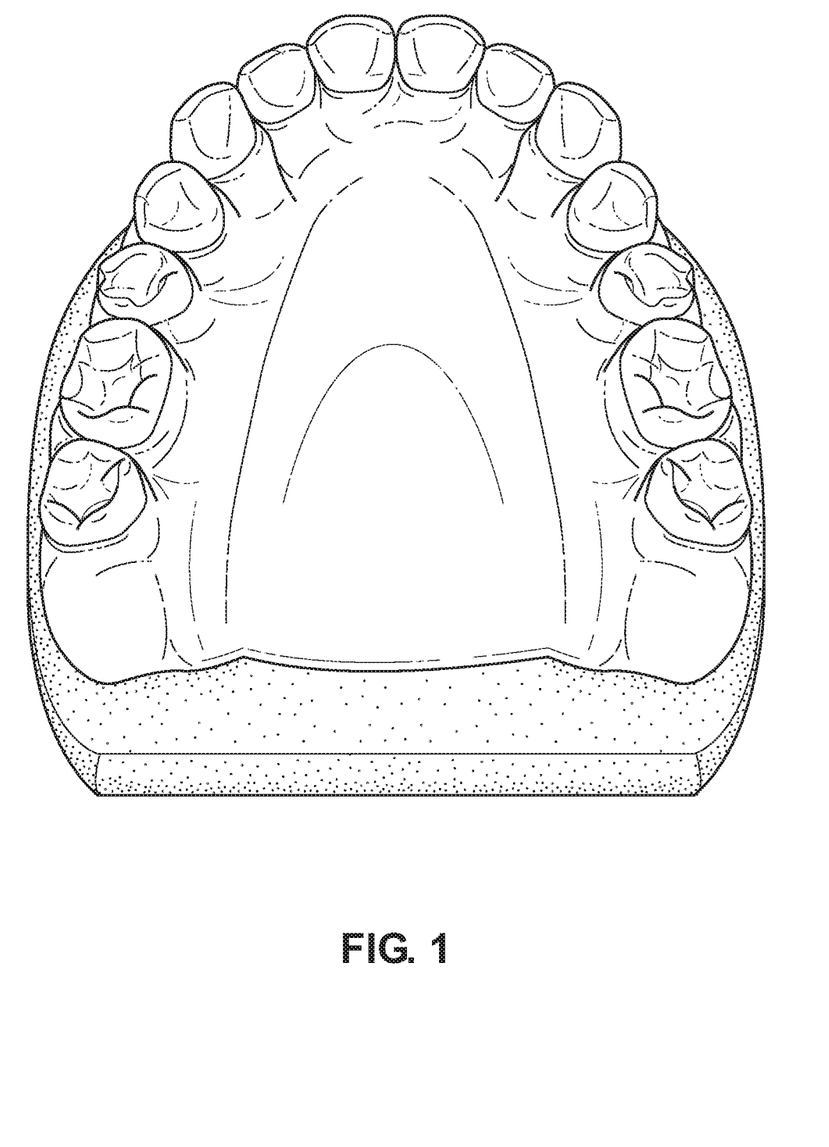
FIG. 1 shows a perspective view of a second denture according to one embodiment of the present invention.
Figure 2:
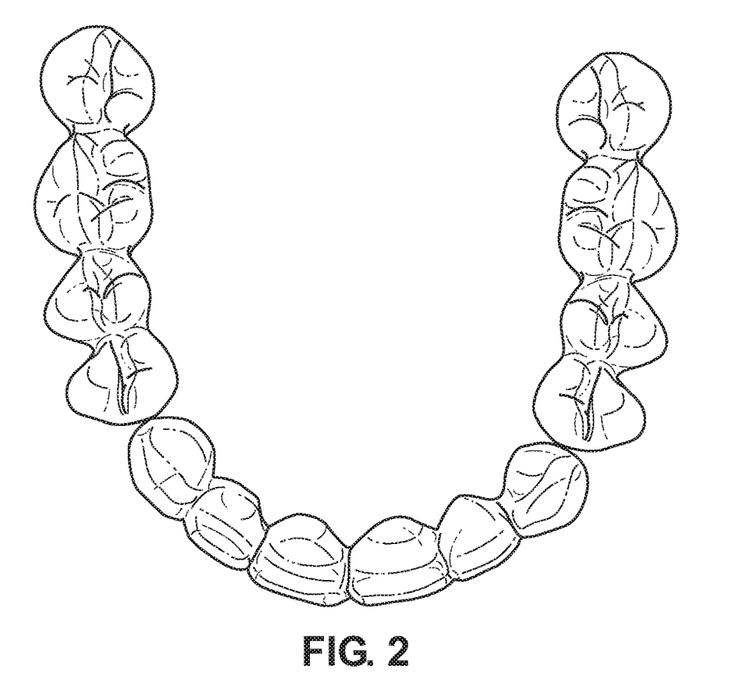
FIG. 2 shows a perspective view of zirconium teeth for a second denture according to one embodiment of the present invention.
Figure 3:
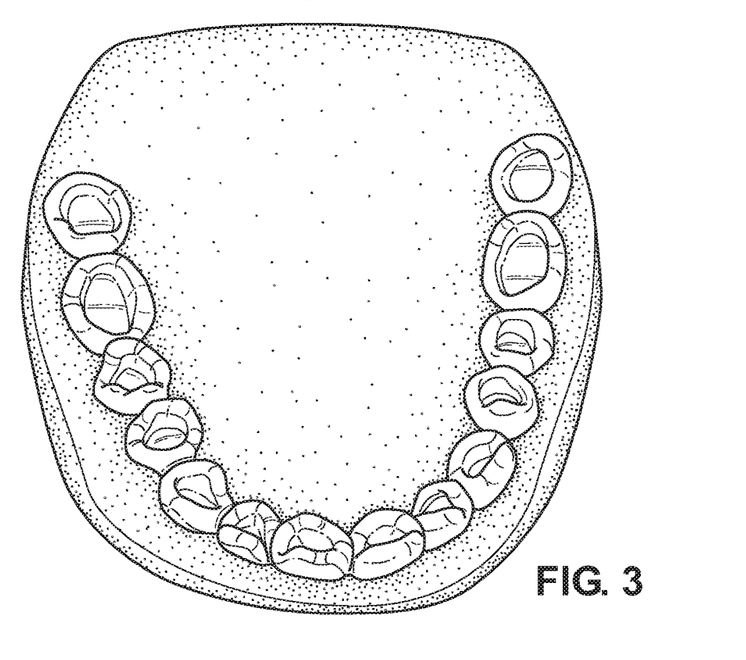
FIG. 3 shows a top view of a first denture according to one embodiment of the present invention.
Figure 4:
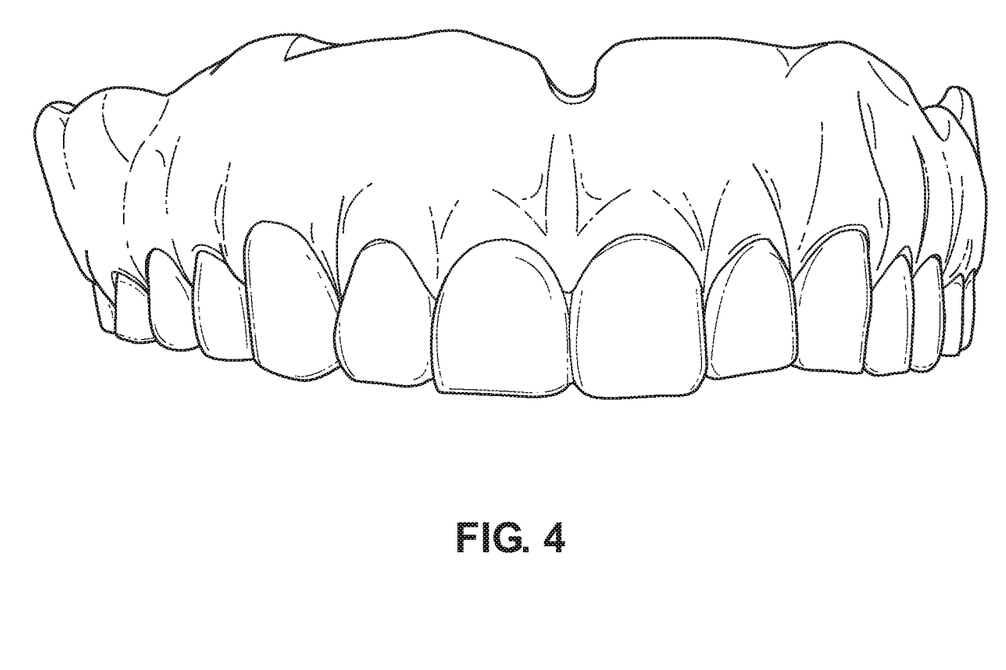
FIG. 4 shows a front view of a denture according to one embodiment of the present invention.
Figure 5A:
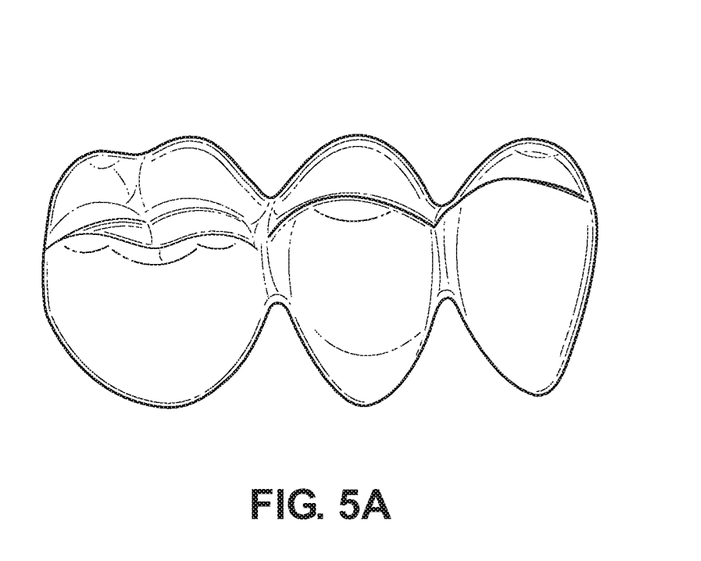
FIG. 5A shows a top view of a zirconia tooth segment member.
Figure 5B:
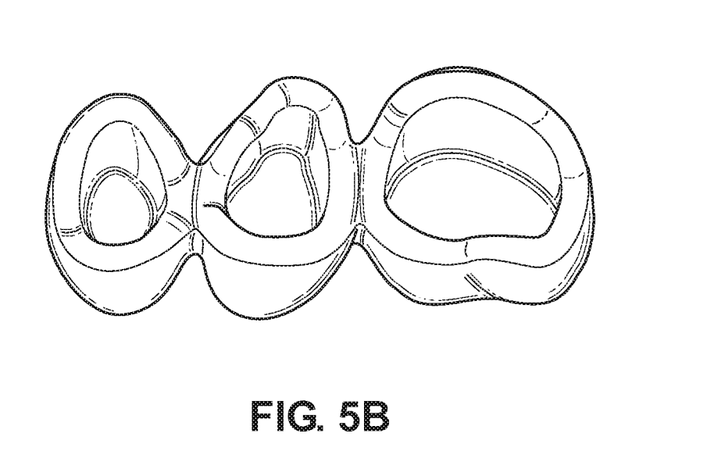
FIG. 5B shows a bottom view of a zirconia tooth segment member.
Figure 6:
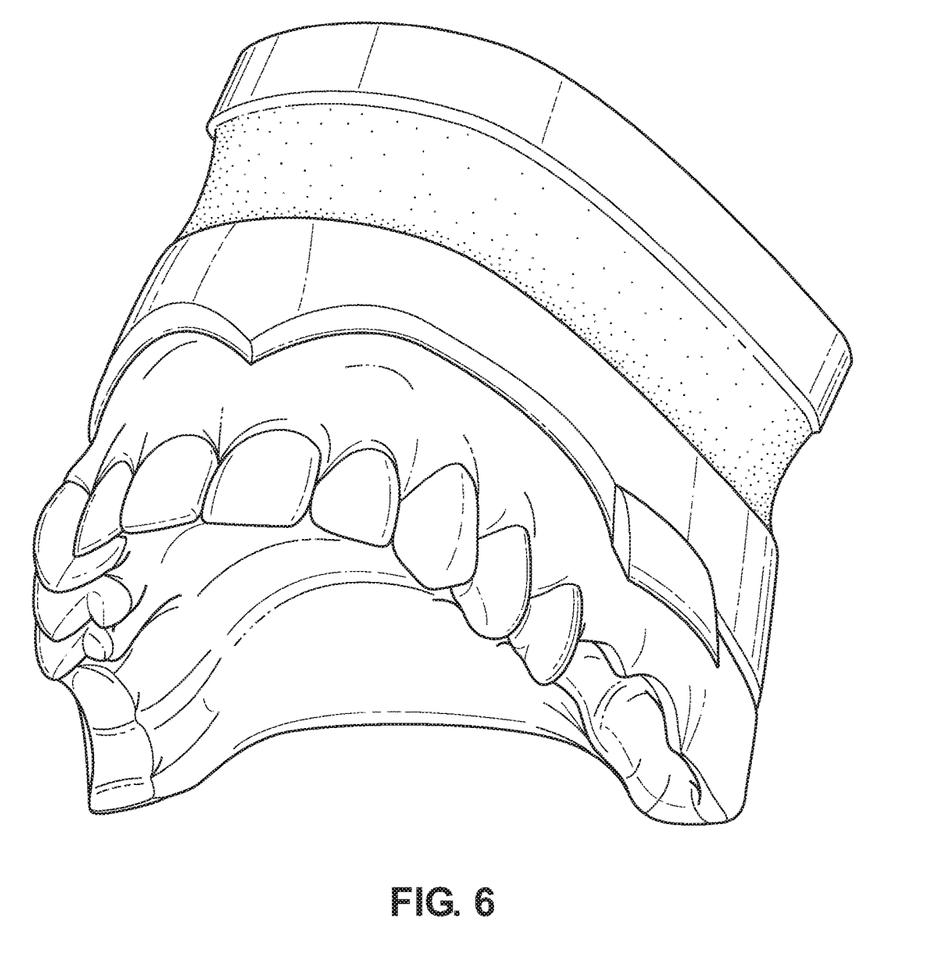
FIG. 6 shows a first denture according to one embodiment of the present invention, after some polymer teeth have been removed.

The present invention teaches a method of manufacturing dentures using zirconia teeth to approximate the look and feel of natural teeth and dentures made by such methods of manufacture. Such dentures have improved wear properties compared to dentures known to the prior art.

Embodiments of the present invention apply equally to full and partial dentures supported by the upper or lower gums, and full or partial bridge dentures supported by existing teeth or implants. In all embodiments, the method and resulting, useable denture made using the method incorporate teeth made of zirconia. Zirconia has high thermal resistance, low thermal conductivity, chemical stability, and high fracture strength. It is a high-performance material with excellent biocompatibility and mechanical properties. Zirconia has extreme hardness and wear resistance. Notably, in laboratory testing, zirconia wears at a rate similar to the wear rate of natural tooth enamel. Zirconia is also colorable and stainable, and can with relative ease be stained to match the esthetics of natural teeth. Zirconia is easily shapeable, and can be readily milled by CAM mills and similar machinery. Zirconia also does not unduly abrade or wear opposing natural teeth.

The first step in manufacturing a denture according to the teachings of the present method is determining the desired parameters of the denture. Parameters include the overall shape and size of the denture and the shape, size, and relative location and orientation of each denture component, including the base, the teeth, and the orientation of the occlusal surfaces of the teeth. Preferably, the desired parameters are all of those parameters that relate to obtaining the desired fit and feel when the denture is used by the patient, preferably a natural bite feel.

The determination of desired parameters is preferably reached through evaluation of the patient by a dentist. This is particularly the case when the desired parameters are those that will result in a natural bite feel. Methods of evaluation the patient to determine the desired parameters are well known to the art, and result in the generation of a substantial amount of information about the patient's landmark oral structures, resting jaw position, muscle, jaw, and tooth movement during normal mastication and speech, the spacing and orientation of teeth, and general bite registry and occlusion characteristics. Approximating these parameters when a denture is in use is, as known to those skilled in the art, essential to preserving the preferred and desired natural bite feel.

As known to the art, the dentist may use a haptic bite pad or other electronic device to obtain computer assistance in calculating the desired parameters and modeling the desired denture, from which a physical denture may be made using known techniques such as CAD/CAM or 3D printing. Alternatively, a dentist may evaluate the patient using known methods, may determine desired parameters based on that evaluation with or without computer assistance, and may input selected data or parameters into a CAD or similar computer modeling program to generate a three-dimensional model of the desired parameter denture, from which a physical denture may be made using known techniques such as CAD/CAM milling, manual milling, or 3D) printing. Preferably, the dentist evaluates the patient using known methods, determines desired parameters based on that evaluation with or without computer assistance, and those parameters are used to by the dentist or a denturist to create a physical denture. This physical denture, whether created in the preferred manner or by some other method, will be referred to as a "first denture," The first denture may be in whole or in part a wax trial denture, or may be made of acrylic or plastic.

After evaluation of the patient and determination of the desired denture parameters, the next step herein is to fabricate a first denture. A first denture according to the teachings of this invention comprises a base portion with a first side configured to overfit at least a portion of the patient's gums, or optionally one or more of the patient's existing teeth or implants, and a second side comprising one or more sockets configured to contain artificial teeth. This base portion is typically made of acrylic, but can also be made of wax. The base portion can be purchased commercially and optionally modified, or, preferably, can be made from stock materials by known methods, such as by CAD/CAM, 3D printing, or by hand, to match as closely as possible the desired parameters.

The step of fabrication of the first denture further includes selecting and inserting artificial teeth into the sockets. These artificial teeth can be custom fabricated, printed, or molded to approximate or match the desired parameters, or can be purchased commercially. In preferred embodiments hereof, such artificial teeth are made of plastic, most preferably polymethylmethacrylate plastics. The denture base and artificial teeth in dentures of the present invention are selected and shaped to result in a first denture approximating the desired parameters, particularly occlusal parameters. In one embodiment, different types of teeth, such as canines, incisors, molars, and the like, will be inserted at different selected locations on the denture base. Alternatively, tooth segment members representing the body and occlusal surfaces of more than one tooth, may be used in lieu of individual teeth. As will further be appreciated, the specific size and shape of each artificial tooth or tooth segment member is selected to conform to the desired parameters, in light of the size and shape of the denture base. The artificial teeth or tooth segment members are not permanently attached to the denture base during this step.

The fabricated first denture comprises at least one occlusal portion. The occlusal portion, as that term is used herein, refers to that portion or portions of the surface of the attached artificial teeth or tooth segment members that is anticipated to form an occlusal surface when the patient uses the denture. The location of the occlusal surface or surfaces will, as would be appreciated, vary on a patient by patient basis depending on the particular characteristics of that patient's oral structures, jaw, jaw musculature, and teeth. Also, depending on whether the denture is upper or lower, whether it is full or partial, and whether it is supported by the gums or by existing teeth or implants, the denture may have one occlusal portion, or may have more than one occlusal portion.

After fabrication of the first denture, its three-dimensional size and shape is determined and stored electronically, preferably by use of a CAD scanner in conjunction with a CAD software program. Alternatively, the size and shape of the first denture may be manually inputted into a CAD program or drawn using CAD based on manually determined measurements.

In one embodiment of the present invention, the first denture is then prepared formation into a useable second denture first by discarding the artificial teeth or tooth segment members used to form the first denture. This leaves a denture base selected and shaped to approximate or match the desired parameters, particularly occlusal parameters.

In this embodiment, the denture base must be sized and shaped to, as closely as possible, create an ideal occlusal relationship when zirconia denture teeth or zirconia denture tooth segment members are mated to it. As would be appreciated by one skilled in the art, failure of the first denture to be sized and shaped to create an ideal occlusal relationship dramatically increases the odds that the second denture provided to the patient will not have a satisfactory fit and feel.

This first denture base may be reused as the denture base for the second denture. Alternatively, the first denture base may be used as a model and replicated in the same or a different material, with such replicate forming the base for the second denture. Still alternatively, the first denture base may be used as a model, and the base for the second denture may be formed from the same or different material in an altered size, shape, or configuration, such differences in size, shape, or configuration adapted to ensure that the second denture teeth or tooth segment members have the desired occlusal relationship, bite, and feel. Such alterations to the denture base may be may, for example, as a result of trial-fitting the first denture, or may alternatively be made due to anticipated differences in the size, shape, or configuration of the first denture teeth or tooth segment members and the second denture teeth or tooth segment members. In a preferred embodiment, for example, the first denture base is embedded into a gypsum form and the wax is eliminated and replaced by an injected polymer or acrylic, according to methods known to the art.

Teeth for the second denture must be created. Custom sized and shaped zirconia teeth or zirconia tooth segment members are prepared to be fitted to the denture base. Preparation of the zirconia teeth or tooth segment members includes selecting zirconia stock based on desired color and esthetic characteristic, and forming and shaping each of the selected zirconia teeth or tooth segment members. As will be appreciated by one skilled in the art, the teeth or tooth segment members selected can represent all of the upper or lower teeth, in the case of a full denture, or less than all teeth, in the case of a partial denture. As will be appreciated by one skilled in the art, different categories of zirconia teeth, such as canines, incisors, molars, and the like, can be created for insertion at different selected locations in the denture base, or tooth segment members representing multiple of such teeth can be created for selected locations in the denture base. Each zirconia tooth or tooth segment member is custom-shaped to conform to the desired parameters, in light of the size and shape of the denture base, when attached to the denture base. The initial size and shape of the zirconia teeth or tooth segment members is selected so that when the zirconia teeth are completely prepared and fitted to the denture base, the result is a second denture with an overall shape, size, and parameters that match the desired parameters.

In this embodiment, the zirconia teeth or tooth segment members are preferably formed by CAM milling from zirconia stock, most preferably by a CAM mill guided by the CAD electronic three dimensional model of the first denture such that the zirconia teeth or tooth segment members are shaped on one side to mate with the denture base and shaped on the other side to form tooth surfaces, including occlusal surfaces, that result in a second denture with the desired parameters. The CAM mill may be directed to form zirconia teeth or tooth segment members of the shape and profile shown by the electronically stored three dimensional image, but oversized to account for shrinkage of the zirconia during the preferred sintering step. Preferably in this embodiment, zirconia teeth or tooth segment members are each thrilled approximately 15% to approximately 20% oversized, with the precise degree of oversizing contingent on the specific sintering conditions intended to be used. Most preferably, the zirconia teeth or tooth segment members are each formed approximately 17.8% oversized.

Preferably in this embodiment, the step of preparing the zirconia teeth or tooth segment members includes sintering each zirconia tooth or tooth segment member after forming. Sintering improves the properties of zirconia for use as an implant, and particularly improves flexural strength, as would be appreciated by one skilled in the art. Sintering for zirconia used in implants is typically performed at temperatures between 1,300 degrees Celsius and 1,700 degrees Celsius, with the greatest improvement in flexural strength occurring at around 1,500 degree Celsius. In preferred embodiments of the present invention, sintering is performed at temperatures of approximately 1,500 degrees Celsius. Time of sintering is dependent on volume, temperature, and method. Although microwave sintering, conventional sintering, and other sintering methods may be used, the zirconia tooth or teeth of the present invention is preferably sintered using conventional sintering for between approximately 8 and approximately 12 hours, and most preferably for approximately 10 hours.

Optionally in this embodiment, the step of preparing a zirconia tooth or tooth segment member may include staining the zirconia tooth to a desired shade, color, or tone, such as to match or simulate real teeth. Such staining, as would be appreciated by one skilled in the art, may occur at virtually any stage of the method. Preferably, staining occurs during sintering.

In this embodiment, after the zirconia teeth or tooth segment members are prepared, each prepared tooth or tooth segment member is attached to the denture base by mating the tooth or tooth segment member with the base to form a second denture that as closely as possible approximates the desired parameters. It should be noted that the second denture is not necessarily a separate structure in this embodiment from the first denture; it is preferably a revision of the first denture created by the replacement of selected polymer teeth or tooth segment members in the first denture with custom sized and custom shaped zirconia teeth. If one or more zirconia teeth or tooth segment members does not obtain the desired fit within the denture base or does not result in a second denture that adequately approximates the desired parameters, one or more zirconia teeth or tooth segment members may be selectively removed and may undergo further preparation. Such flirter preparation may include, by way of example, additional sintering, milling, sanding, abrading, cutting, or other shaping.

In this embodiment, after the one or more zirconia teeth or tooth segment members are determined to be suitably prepared, they may be permanently attached to the demure base. Preferably, however, the prepared zirconia teeth or tooth segment members are first removably inserted into the denture base for test-fitting with the patient. During test-fitting the dentist may assess whether the second denture creates the desired fit and feel for the patient, preferably a natural bite feel. The dentist may assess the patient objectively, including recording occlusal patterns or data. The dentist may separately or additionally solicit or accept subjective feedback from the patient concerning the fit and feel of the second denture. Based on this further assessment, the denture base, or one or more of the zirconia teeth or tooth segment members, or all of the foregoing, may be further shaped or altered responsively to the assessment, including the patient's preferences and the dentist's judgment of the patient's needs. This test-fitting and revision process may, as would be appreciated, be repeated until the second denture creates a fit and feel satisfactory to the patient and the dentist. This further test-fitting and further evaluation step may optionally and preferably be completed after the formation of one or more zirconia teeth or tooth segment members, but before the sintering substep.

In a preferred embodiment, each zirconia teeth or tooth members are formed so that the side of the tooth or tooth segment member that interfaces with the base to lock mechanically with the base. Preferably, the zirconia teeth or tooth members are formed with a lockable cavity, into which an acrylic denture base can be processed in liquid form such that when the acrylic hardens, a mechanical lock is formed between the denture base and each tooth or tooth segment member. In this preferred embodiment, each prepared zirconia tooth or tooth segment member is attached to the denture base and permanently affixed thereto to create a second denture through the use of injection molding processes known to the art. In this preferred embodiment, the prepared zirconia tooth or tooth segment members are inserted into a wax first denture base. The wax first denture base is then embedded into a gypsum form and the wax first demure base is eliminated and replaced by injected acrylic, as would be appreciated by one skilled in the art, to form a second denture. When such injected acrylic is processed into the base of zirconia teeth or tooth segment members formed according to the teachings of this preferred embodiment, a mechanical lock is formed between the acrylic second denture base and said zirconia teeth or tooth segment members.

After the second denture is determined to be satisfactory to the patient and the dentist—which preferably but optionally includes the further assessment discussed above—the second denture is finished. In embodiments where a second acrylic denture is not processed by injection into the tooth or tooth segment bases, the one or more zirconia teeth or tooth segment members are stained, if staining is desired and has not yet been performed, and are sintered, if sintering is desired and has not yet been performed. In these embodiments, the second denture base may at this point be permanently attached to the denture base. In these alternate embodiments, such permanent attachment can be accomplished through the use of adhesives or resins, using techniques known to the art, by cleaning each zirconia tooth and the denture base with a solvent such as alcohol, applying a first primer to the surface of the zirconia tooth that will contact the surface of the denture base, applying a second primer to the area of the surface of the denture base that will contact the surface of the zirconia tooth, applying a bonding agent such as a dual-cure resin cement to both surfaces, attaching the zirconia tooth to the denture base in the desired position and orientation, extravagating excess bonding agent, and allowing the bonding agent to finish curing. A wide variety of adhesives and adhesive attachment techniques may be used within the scope and spirit of this invention.

In the preferred embodiment in which an acrylic denture base is processed into the zirconia teeth or zirconia tooth segments to form a mechanical lock, sintering and/or straining of the zirconia teeth or zirconia tooth segments is also preferred. However, in this preferred embodiment, the sintering and/or staining steps must occur prior to the injection of the acrylic denture base, due to the heat involved. In this preferred embodiment, the step or steps of sintering and/or staining may occur at any time after formation of the zirconia teeth or zirconia tooth segments and before processing of the acrylic denture base into the teeth or tooth segments.

Although the present invention has been described in considerable detail with reference to certain preferred versions thereof, other versions are possible. For example, materials, shapes, sized, or configurations other than those described in detail herein may be used for the versions of this invention. Further, the method may include additional steps, intervening steps, or steps performed in an order other than those specified in the embodiments described above. Therefore, the spirit and scope of the claims should not be limited to the description of the preferred embodiments described herein.

What is claimed is:

1. A method for making an artificial full or partial denture with natural bite and wear properties, said method comprising the steps of:
   a. Evaluating a patient to determine desired denture parameters;
   b. Fabricating a first denture according to those desired denture parameters, the first denture including a denture base and one or more polymer denture teeth or polymer denture tooth segments;
   c. Electronically storing the three-dimensional shape and size of the first denture;
   d. Discarding said one or more polymer denture teeth or polymer denture tooth segments;
   e. Preparing one or more zirconia denture teeth or zirconia denture tooth segments, where the one or more zirconia denture teeth or zirconia denture tooth segments are collectively sized and shaped to create a denture approximating the desired denture parameters when mated to the denture base; and
   f. Attaching said one or more zirconia denture teeth or zirconia denture tooth segments to said denture base to create a useable second denture, where the second denture approximates said desired denture parameters.

2. The method of claim 1, further comprising the steps of:
   a. Test fitting said second denture to the patient;
   b. Assessing the patient; and
   c. Shaping one or more of said zirconia denture teeth, zirconia denture tooth segments, or denture base, responsively to said assessment.

3. The method of claim 2, further comprising the step of permanently attaching at least one zirconia denture tooth or zirconia denture tooth segment to said denture base.

4. The method of claim 3, further comprising the step of mechanically locking at least one zirconia denture tooth or zirconia denture tooth segment to said denture base.

5. The method of claim 3, wherein said step of preparing said at least one zirconia denture tooth comprises at least one of milling, cutting, and forming at least one zirconia denture tooth.

6. The method of claim 3, wherein said step of preparing said at least one zirconia denture tooth segment comprises at least one of milling, cutting, and forming at least one zirconia denture tooth segment member.

7. The method of claim 3, wherein said step of electronically storing the three-dimensional shape and size of said first denture comprises storing the three-dimensional shape and size of said first denture in a CAD program.

8. The method of claim 7, wherein at least one of the step of fabricating a first denture and the step of preparing one or more zirconia denture teeth or zirconia denture tooth segments is performed by a CAM mill.

9. The method of claim 8, wherein the step of preparing said one or more zirconia denture teeth or zirconia denture tooth segments comprises the substeps of:
   a. Forming said one or more zirconia denture teeth or zirconia denture tooth segments to a first shape and a first size; and
   b. Sintering said zirconia denture teeth or zirconia denture tooth segments to a first shape and a second size, wherein said first shape and second size are selected to create a second denture approximating said desired denture parameters when said one or more zirconia denture teeth or zirconia denture tooth segments are attached to said denture base at a selected location.

10. The method of claim 9, wherein the sub step of forming said one or more zirconia denture teeth or zirconia denture tooth segments to a first shape and a first size is performed by a CAM mill.

11. The method of claim 10, wherein said first shape and first size are determined using the electronically stored three-dimensional shape and size of said first denture.

12. The method of claim 11, wherein the substep of sintering further comprises sintering said one or more zirconia denture teeth or zirconia denture tooth segments at approximately 1500 degrees Celsius.

13. The method of claim 12, wherein the substep of sintering further comprises sintering said one or more zirconia denture teeth or zirconia denture tooth segments for between approximately 8 and approximately 12 hours.

14. The method of claim 13, wherein the sub step of sintering further comprises sintering said one or more zirconia denture teeth or zirconia denture tooth segments for approximately 10 hours.

15. The method of claim 14, wherein said first size is approximately 15% to approximately 20% larger than said second size.

16. The method of claim 15, wherein said first size is approximately 17.8% larger than said second size.

17. A custom denture with desired parameters, said denture comprising:
   a base portion configured to overfit at least a portion of a patient's gums, said base portion comprising one or more sockets;
   one or more zirconia denture teeth or zirconia denture tooth segments attached to one or more of said sockets, at least one of said zirconia denture teeth or zirconia denture tooth segments custom-made based on desired parameters.

18. The custom denture of claim 17, wherein said custom denture is a full denture.

19. The custom denture of claim 18, wherein said custom denture is a partial denture.

* * * * *